United States Patent
Magne et al.

(10) Patent No.: US 9,527,087 B2
(45) Date of Patent: Dec. 27, 2016

(54) REAL-TIME MONITORING SYSTEM TO DETERMINE WEAR OF GRATE RIBS IN SEMI-AUTOGENOUS MILLS, TO DETECT CLOGGING CONDITIONS OF THE GRATES DURING THE OPERATION AND TO DETECT WORKING CONDITIONS UNDER DIRECT IMPACT OF THE BALLS ON THE GRATES

(71) Applicant: Universidad de Santiago de Chile, Santiago (CL)

(72) Inventors: Luis Magne, Santiago (CL); Gilda Titichoca, Santiago (CL); Eduardo Altamirano, Santiago (CL); German Sepulveda, Santiago (CL); Marcelo Vasquez, Santiago (CL)

( * ) Notice: Subject to any disclaimer, the term of this patent is extended or adjusted under 35 U.S.C. 154(b) by 520 days.

(21) Appl. No.: 13/916,302

(22) Filed: Jun. 12, 2013

(65) Prior Publication Data

US 2014/0150524 A1    Jun. 5, 2014

Related U.S. Application Data

(63) Continuation of application No. PCT/IB2011/003039, filed on Dec. 14, 2011.

(30) Foreign Application Priority Data

Dec. 14, 2010   (CL) .................................. 1433-2010

(51) Int. Cl.
   *G01M 1/14*    (2006.01)
   *B02C 17/18*   (2006.01)
   (Continued)

(52) U.S. Cl.
   CPC ........... *B02C 17/1805* (2013.01); *B02C 17/22* (2013.01); *G01N 29/12* (2013.01)

(58) Field of Classification Search
   CPC ...... B02C 17/1805; B02C 17/22; G01N 29/12
   See application file for complete search history.

(56) References Cited

U.S. PATENT DOCUMENTS

| 5,159,312 A | * | 10/1992 | Engle | ........................ | B60D 1/60 |
|---|---|---|---|---|---|
| | | | | | 307/9.1 |
| 5,264,368 A | * | 11/1993 | Clarke | .................. | G01M 3/047 |
| | | | | | 250/301 |

(Continued)

FOREIGN PATENT DOCUMENTS

| WO | WO 2012/080817 A2 | 6/2012 |
|---|---|---|
| WO | WO 2012/080817 A3 | 6/2012 |

OTHER PUBLICATIONS

PCT "International Search Report and PCT Written Opinion of the International Search Authority" of Jun. 12, 2012 for International Application No. PCT/IB2011/003039, WO 2012/080817 A3 published Jun. 21, 2012 of Universidad de Santiago de Chile.

*Primary Examiner* — John Fitzgerald
*Assistant Examiner* — Truong Phan
(74) *Attorney, Agent, or Firm* — Tolpin & Partners, PC; Thomas W. Tolpin (57) ABSTRACT

A real-time monitoring system to monitor the wearing in the thickness of the ribs (5) of a grate (1) of a SAG mill (9) due to the abrasive action of the ore pulp residing inside the mill and due to the action of the grinding elements during the operation, and which in certain cases also generates obstruction of the slots (4) due to the jamming of said grinding elements inside the slots (4) while the mill is running, and said grate (1) has a screening surface (2) that includes a pulp lifter (3) and an external surface (7) that is not exposed to impacts, and also includes a central trough (6) where the supporting elements fit and which allow securing the grate inside the mill through fitting bolts (12), wherein said system includes: a sensor (16) located on the external surface (7), (Continued)

and said sensor (16) is connected to a sensor adaptor unit (17); a wireless transmitter (18) connected to said sensor (16), and said transmitter transmits the signal from the sensor (16); a wireless receiver (20) receiving the signal from the wireless transmitter (18); and a signal reader (21) connected to said wireless receiver (20) which processes the signals received from the accelerometer. The sensor (16) can be an accelerometer or a strain gage.

15 Claims, 10 Drawing Sheets

(51) Int. Cl.
     *B02C 17/22*     (2006.01)
     *G01N 29/12*     (2006.01)

(56) References Cited

U.S. PATENT DOCUMENTS

| | | | |
|---|---|---|---|
| 5,698,797 | A | 12/1997 | Fontanille et al. |
| 6,252,334 | B1 * | 6/2001 | Nye .................. B64G 1/222 310/316.01 |
| 6,874,364 | B1 * | 4/2005 | Campbell .......... B02C 17/1805 73/593 |
| 7,172,144 | B1 | 2/2007 | Slater et al. |
| 2002/0033425 | A1 | 3/2002 | Sellars |
| 2004/0255680 | A1 * | 12/2004 | Ortega ............... B02C 17/1805 73/649 |
| 2006/0248676 | A1 * | 11/2006 | Baek .................. A47L 9/1436 15/319 |

* cited by examiner

REAL-TIME MONITORING SYSTEM TO DETERMINE WEAR OF GRATE RIBS IN SEMI-AUTOGENOUS MILLS, TO DETECT CLOGGING CONDITIONS OF THE GRATES DURING THE OPERATION AND TO DETECT WORKING CONDITIONS UNDER DIRECT IMPACT OF THE BALLS ON THE GRATES

TECHNICAL FIELD OF THE INVENTION

The present invention relates to a real time monitoring system for thickness of ribs, detecting undesired impacts on a grid, and obstructing the slots in grates of Semi-Autogenous mill (SAG), while the latter is in operation. The main feature in the system operation is the detection and analysis of the natural vibration frequency in the ribs of the grates and its relationship with the thickness of the ribs thereof, as well as the condition of rigidness generated when the slots are obstructed with the means of the grinding. The system mainly consists of: a vibration sensor; a module for wireless data transmission; and receiving module for that signal. As the vibration sensor is inserted in side the SAG mill to retrieve the measurements; such action results in the fact that the sensor should have certain features both in terms of frequency as in a maximum capacity to endure impacts. This system also allows detecting conditions of direct impact from the balls on the grates thus facilitating adopting actions to remove this working condition—or minimize it, as to prevent cracking of the grates thereof.

BACKGROUND OF THE INVENTION

During a SAG mill operation as with other components within thereof, the grates experience wearing due to the movement of the internal load which generates abrasive actions on the liners as well as direct impacts from the elements used for the grinding operation, i.e., the steel balls. On the other hand, during the operation of the mill and the variations in the content of the internal loading, due to the effect of the granulometry of the ore fed or ore hardness, variations are generated in the composition of the internal load. If these variations mean a decrease in the ratio of ore inside thereof, there is a greater amount of mill balls inside thereof, thus explaining the mechanical demand on the components, particularly grates as they are subject to an excess of impacts from the elements designed to hit the ore. This condition might result in the impacts between balls and the grate produce an even greater wearing than the usual or that they reach a level of structural resistance thus producing fracture of such elements, especially during the last stage of their working life.

Fracture in a discharge grate forces stoppage of the mill for periods ranging from four to twelve hours (or more), depending on the size of the mill and the degree of damage produced to the components, which has the impact of significant production losses.

Controlling the conditions of such components in mill liners is performed by stopping the mill as to carry out the inspection, which generates an important loss in production. During such stoppages the condition of the elements are visually checked and the thickness of the grates ribs is measured as to determine the remaining useful life.

During said inspections, it is possible to find situations of clogging in the discharge grates as the balls are embedded in between the grate slots preventing the ore ground to the size of the slot to be discharged via the normal ways in the process. This condition is reflected in the decrease in the treatment capacity of the mill due to the increase in the retention time of the ore thereof, which translates in important production losses.

A number of attempts had been made in the state of the art aiming to provide real-time monitoring of the conditions under which the milling is being done while the mill is under operation. For example, in U.S. Pat. No. 6,874,364 (Campbell et al.) published on Apr. 5, 2005, discloses a system to monitor mechanical waves in a machine that has particles in motion when in operation, wherein the system includes at least a sensor located in the machine at a distal location from the central axis of the machine, and the sensors are designed to detect acoustic waves and include a transmitter to transmit signals representing the mechanical waves detected to a receiver located in a remote location from the sensor(s), a data processor connected to the receiver to receive signal from the receiver representing the mechanical waves and to process signals as to produce output signals for further visualization in a screen, where the output signals represent one or more parameters indicative of the mechanical waves produced by the machine during a specific period of time.

Document U.S. Pat. No. 5,698,797 (Fontanille et al.) published on Dec. 16, 1997, discloses a monitoring device for a ball mill which has a group of balls arranged, during the rotation of the mill at a normal speed, between two generators (Ib, Ib) separated to a minimum angle ($\alpha$) and a maximum angle and a mass of coal arranged during the rotation of the mill at a normal speed between two generator (Ic, Ic) separated in an angle ($\beta$), and which consists of a wave transmitter, waves selected from between the electromagnetic waves, wherein said transmitter can be arranged within the mill, and receiver means for such waves, wherein said receiver means are connected to an electronic circuit to determine the parameters corresponding to the number of balls, the amount of coal, and the wearing of the cover, where such means can be arranged in the external part of the mill in such a way that they can detect the waves crossing a generator Ib and the waves in the external part of the maximum angle sections and $\beta$, as to determine the wearing of the cover; and that they can detect the waves in the angle section $\beta$ not common to the angle section in order to determine the amount of coal. The wave receiver means are arranged in a rotational manner around the longitudinal axis of the cover in an angle section above the angle section encompassing $\alpha$ and $\beta$. 3. In this system the transmitter is located in the longitudinal axis of the cover whereas such transmitter is a gamma-ray photon type transmitter. The electronic circuit to determine the number of balls include, for each generator (Ib, Ib), one converter and one lineariser, wherein the signals from each lineariser are associated as to calculate the number of balls. The electronic circuit to determine the wearing in the case consists of a converter connected to a device to read the degree of wearing.

Document DE 4215455 (Godler) published Nov. 18, 1993, discloses a system with sensors for sound signals produced as a response to the noise generated by the milling plant, signals that are then analyzed as to render a measurement value of the status of operation of the plant. The status of the operation is measured as per the level of the mill. In order to analyze the noise, the system creates a noise spectrum and includes a device for a fast Fourier transformation. It also includes a device that creates the average of the spectrum during a long period of time. This system allows determining the performance of the mill, particularly a mill for rocks, in order to improve it and to improve the quality of the processed material.

The three documents described above disclose methods and apparatus that detect noise and make the correlation of said noise as to determine some of the operation properties. However, none of said documents teach how to detect the thickness in the ribs of a SAG mill discharge grates, and not even how to place them within the mill thereof.

BRIEF SUMMARY OF THE INVENTION

Based on the above, the object of this invention is to provide a monitoring system that allows determining: thickness of the ribs, conditions of undesired impacts on the grates, and obstruction in the slots of the grates in a SAG mill for milling ore, while said mill in operation.

Other object of this invention is to detect conditions where the balls hit the grates directly in order to take actions to remove this working condition—or minimize it.

A more detailed explanation of the invention is provided in the following detailed descriptions and appended claims taken in conjunction with the accompanying drawings.

BRIEF DESCRIPTION OF THE DRAWINGS

The drawings herein, which are included as to provide better understanding of the invention, are an integral part of the description and also illustrate part of the previous art as well as some of the preferred embodiments and are used as a way of explanation of the principles of the invention.

DETAILED DESCRIPTION OF THE INVENTION

The following is a detailed description and explanation of the preferred embodiments of the invention and best modes for practicing the invention.

The present invention relates to a real time monitoring system to determine the thickness of the ribs in the grate of SAG mill, detecting undesired impacts during the operation, and obstruction in the slots thereof, while the mill is in operation. The operation of the system is mainly based on the ratio between the thickness of the ribs and their natural vibration.

Figure 1:
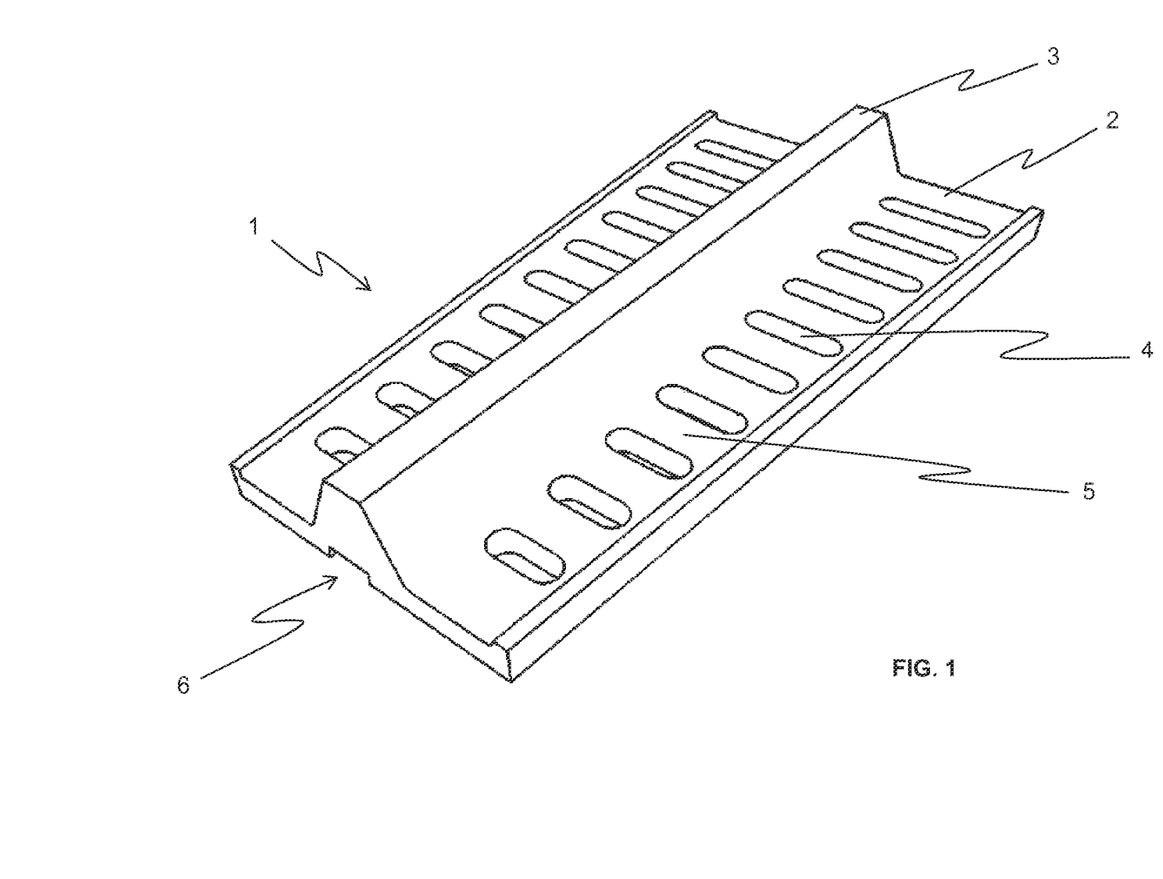
FIG. 1 illustrates a perspective view of the grate showing the front surface or surface of the ore when entering the component, and which is directly in contact with the internal load of the ore and the moving balls.

FIG. 1 illustrates a grate (1) that has a screening surface (2) including a central lifter (3). The screening surface has a plurality of slots (4) with a rib which is integral part thereof, and which has sufficient structural strength to hold the internal load in motion while allowing the ore milled to the size of the opening exits the mill toward the pulp lifter. The ribs (5) generate in-between said slots (4), wherein such ribs are mainly subject to abrasive wearing. When the milling operation is out of control, the milling elements usually impact the surface of the ribs (5). Usually these milling elements are steel balls of large size (presently, up to 6 inches [equivalent to 15.3 cm]) produce the fracture of the ribs. Also, the slots (4) can be obstructed when the balls are jammed thereof, preventing the ore to be discharged from with in the mill.

Therefore it is necessary to provide real-time monitoring to the condition of the slots (4) and the ribs (5).

Figure 2:
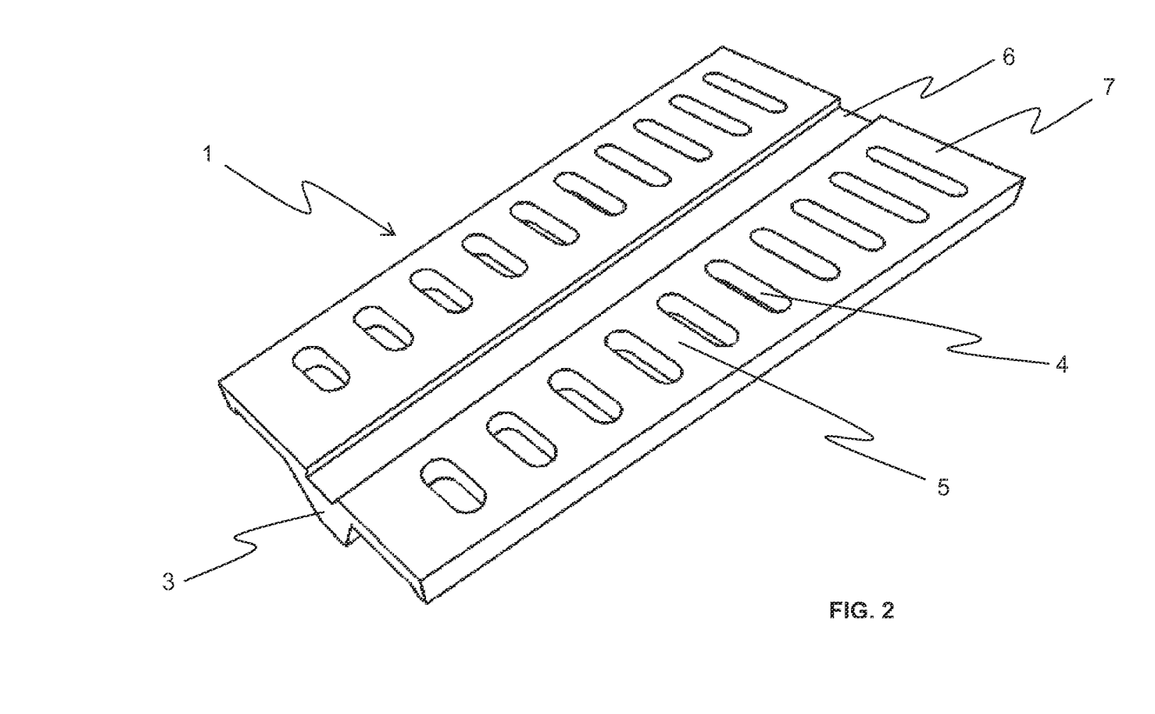
FIG. 2 illustrates a perspective view of the rear side of the grate, which is in contact with the ore that has passed through the slots of the grate and is built up in the pulp lifter to be further evacuated from within the mill.

FIG. 2 illustrates a rear view of the grate (1), showing the external surface (7) of the grate not exposed to impacts. The grates have a central trough (6) that runs axially and where supporting elements are fixed, elements that allow fixation of the grate inside the mill by fitting bolts.

As the external surface (7) is not subject to impacts, it is feasible to place certain type of sensor that allows associating certain type of parameter to the thickness of the ribs (5).

The principle of this invention is based on the fact that if a rib (5) which has a specific thickness is impacted by a steel ball, the rib vibrates within its natural frequency. If the thickness changes, said natural frequency will also change.

In order to detect the vibration frequency of a rib, an accelerometer is used as a vibration sensor. The accelerometer is a transducer that measures the acceleration with which this is affected by any force, and its movement due to this effect.

Generally accelerometers are especially built as to measure types of vibration in objects to which the accelerometers are attached, and not to detect all the surrounding signals as is the case of a microphone. As the acceleration has the same frequencies than the motion producing them, the device can deliver accurate results with different characteristics depending on factors such as intensity of the vibration and vibration frequencies.

The feature mentioned above in accelerometers is possible to generate a relationship between the vibrations and wearing in the rib of a grate.

Based on assays conducted it was possible to compare the relationship factor, Fr, from the vibration for different thickness produced by wearing in the ribs. Below are some examples of the results of such assays:

| Initial thickness percentage | Relationship factor (Fr) |
|---|---|
| 100% (new) | 1 |
| 76.8% | 0.76 |
| 64.2% | 0.66 |
| 57.6% | 0.68 |

With the results obtained it was obvious that there is a relationship between thickness and the relationship factor Fr from the vibration. Using these results it was possible to confirm the existence of a relationship between vibration and rib wearing, therefore it is possible to determine the latter from the former. This allows developing a sensor to measure wearing based on the measurement of vibrations.

Thus, in object to continuously measure rib (5) thickness it is necessary to provide a system within the mill that transmits the vibration in real time as to correlate vibration and thickness, to determine how thickness varies in time when the mill is in operation.

One of the major problems faced when attempting to provide a real-time monitoring system where some of its elements need to be placed inside the mill is the location of said elements.

Therefore in the screening surface (2) of the grate (1) is not possible to place any type of sensor as it would be destroyed by the impacts on said screening surface (2) as it is faced towards the internal load consisting of the ore being milled and the milling elements, i.e. steel balls. Therefore, placement of the sensor is done on the external surface (7) that is not subject to impacts but which vibrates similarly to the screening surface (2).

On the other hand, the vibration sensor can not be placed directly onto the rib as any work to be done on this, for instance, a perforation, to place said sensor would affect the structural strength of the rib (5), thus producing its weakening thereof.

Figure 3:
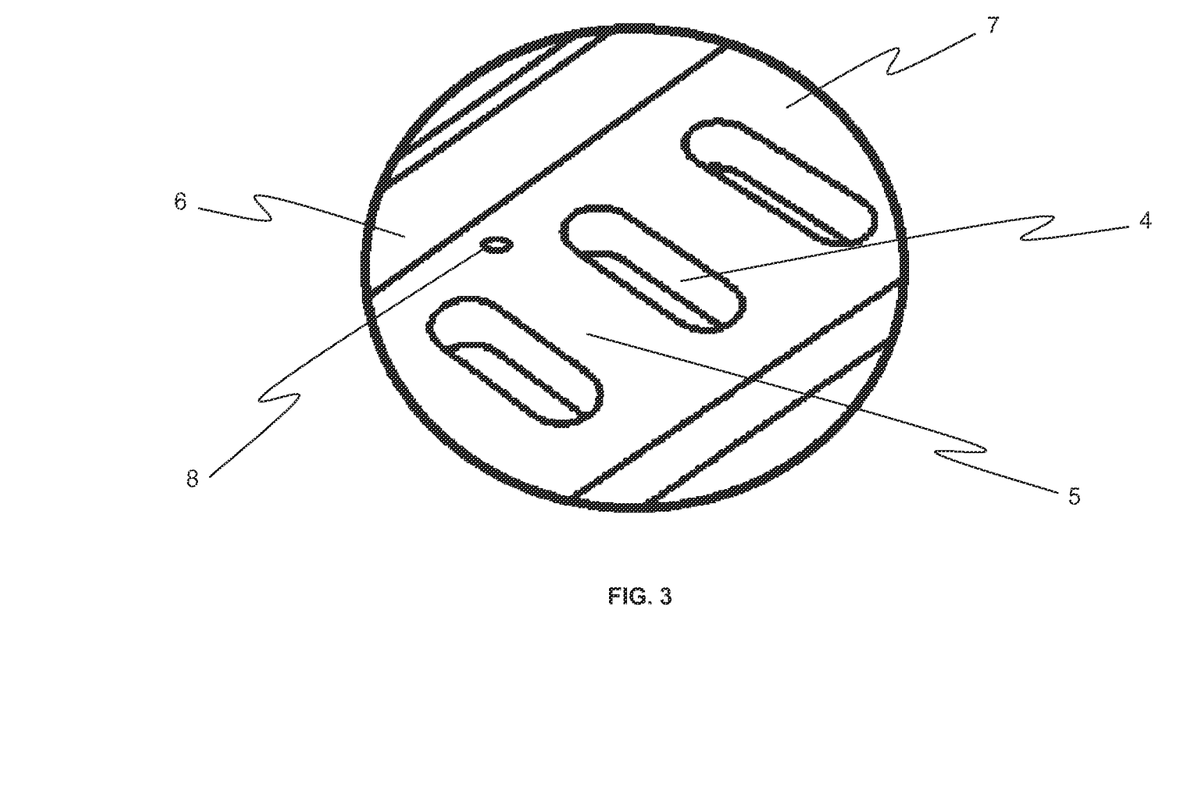
FIG. 3 shows an expanded view of FIG. 2, showing the preferred location of the monitoring system sensor of the present invention.

FIG. 3 shows the preferred location for the sensor of the present invention. This Figure is an expanded view of FIG. 2 showing the external surface (7) of the grate (1). The sensor is placed in the bore (8) located in the base of the rib (5), close to the central trough (6) that matches the supporting elements (22) and which through the use of bolts, allow fixing the grate within the mill.

Figure 4:
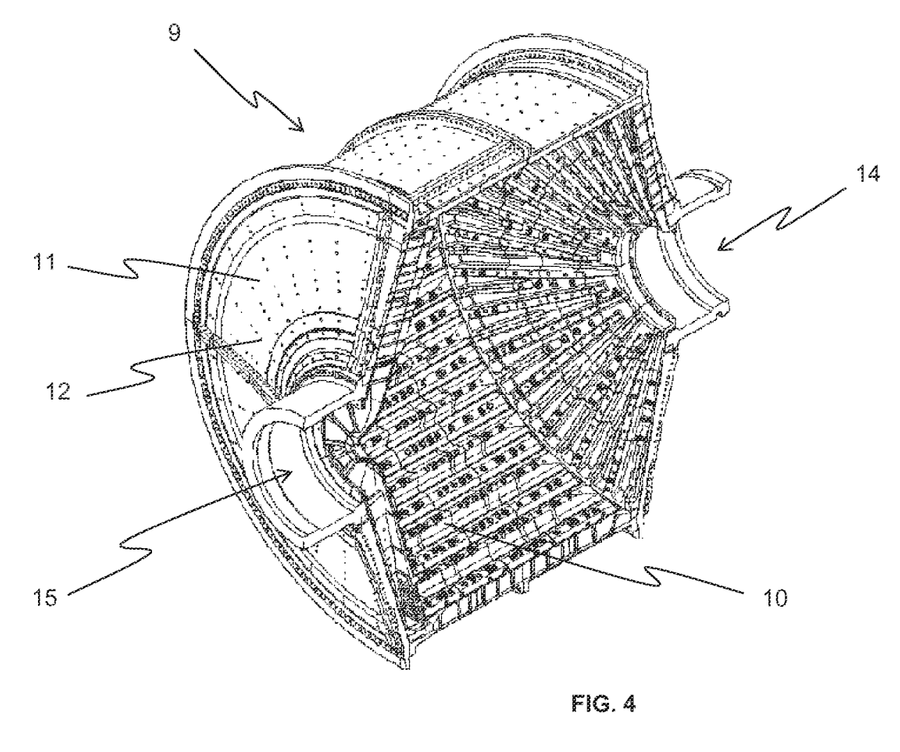
FIG. 4 illustrates a section view of a mill, showing the cover and fitting screws thereof.

FIG. 4 is a cross-section of a mill (9) showing inside (10) liners and lifting elements, also subject to wearing, and which allow that both the ore and the balls rotate, lifting the material up and around thus producing the grinding of the material which enters the opening (14) and which goes out through the exit port (15). The mill (9) has a cover (11) attached to the supporting elements (22) which allow fixing of the grate (1) through bolts (12).

Figure 5:
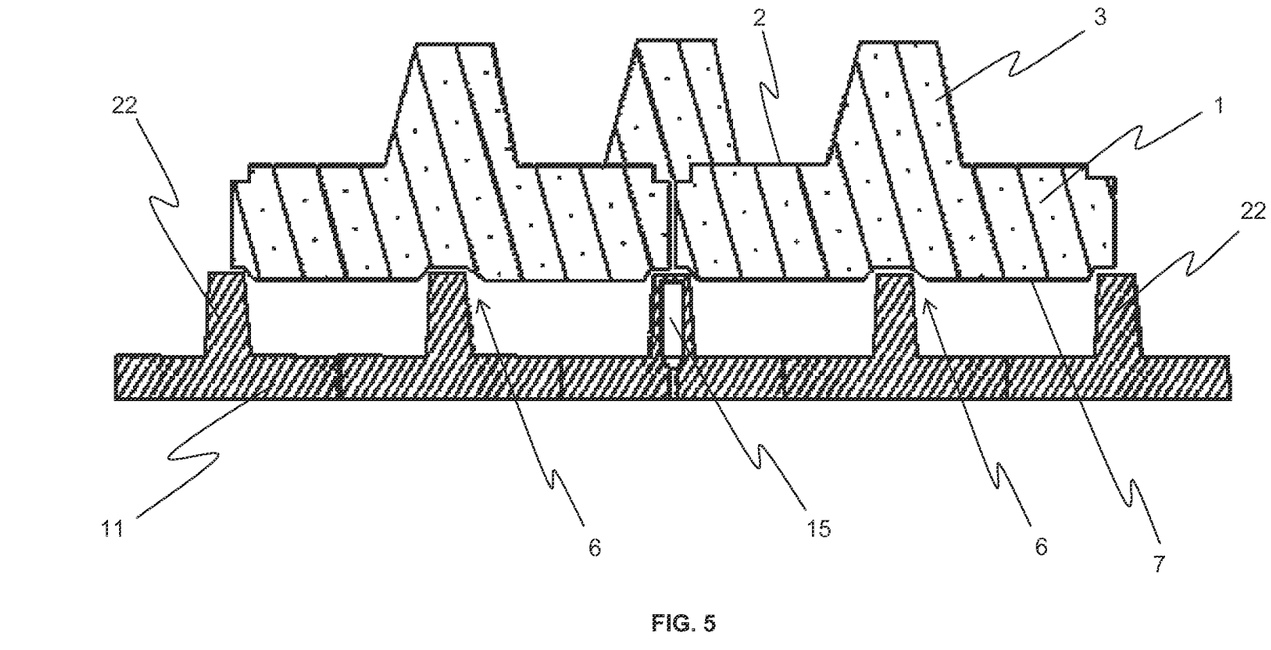
FIG. 5 illustrates a schematic view of a grate and the lid in the semi-autogenous mill for ore milling, with a perforation for one of the fitting bolt of the lid thereof.

As shown in FIG. 5, and considering the explanation provided in the previous paragraph, it is possible to place a sensor on the external surface (7) of the grate (1), which, through the central trough (6) and the supporting elements (22) is affixed by bolts crossing the inner chamber (15) of the supporting elements (22).

Under these conditions it is possible to determine the elements that make up the monitoring system and their location, based on minimizing the risk of destroying the vibration sensor, its wiring, wireless transmitter, and receiver thereof.

Figure 6:
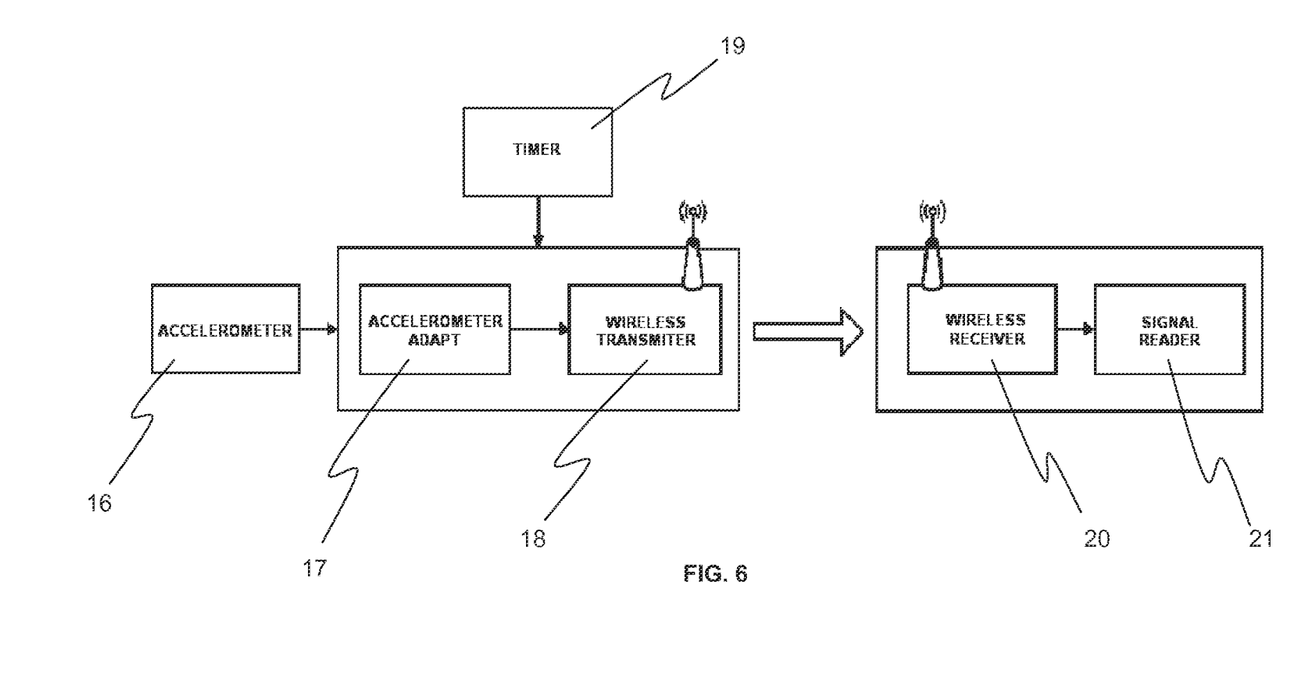
FIG. 6 shows a block diagram of the monitoring system of the present invention.

The modules of the monitoring system in the present invention, as shown in FIG. 6, wherein an accelerometer (16) is connected to the accelerometer adaptor unit (17) which comprises or functions as a transducer and to a wireless transmitter (18) connected to a timer (19). The wireless transmitter (18) issues a signal which is received by the wireless receiver (20) connected to a signal reader (21), normally a PC with a signal reading software. The role of the timer is to help defining the time interval to issue the signals from the transmitter as it is not required that it transmit 100% of the time when the mill is in operation, and only the time interval specified in defined periods (once a day, every two days, every three days, etc.)

Figure 7:
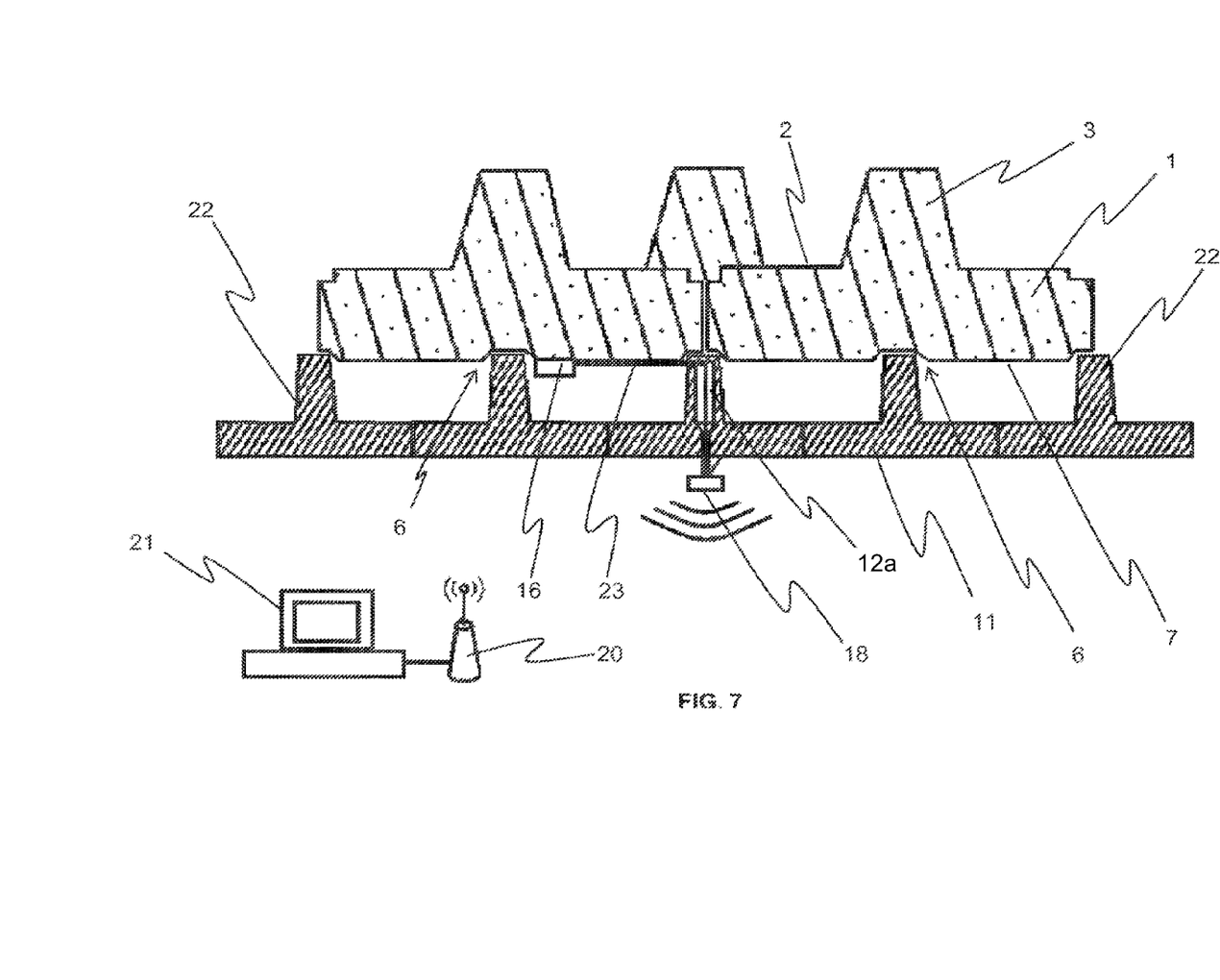
FIG. 7 shows a schematic view of a first location for the monitoring system sensor of the present invention.

In a first embodiment of the present invention as shown in FIG. 7, the signal from the accelerometer (16) is conveyed by wiring (23) located on the external surface (7) of the grate (1), wherein said wiring (23) reaches the trough (6) of the grate to then enter the chamber (15) of the supporting elements (22), wherein said wiring (23) connects the wireless transmitter (18) placed through a bolt hole (12*a*) defining a cavity on the cover (11) of the mill (9), and wherein the wireless signal is output to the wireless receiver (20), where the signal is processed by a signal reader (21), usually a PC with a signal reader software. The wireless receiver (20) can be placed in a safe area outside the SAG mill at a distance of approximately 20 meters from the mill.

Figure 8:
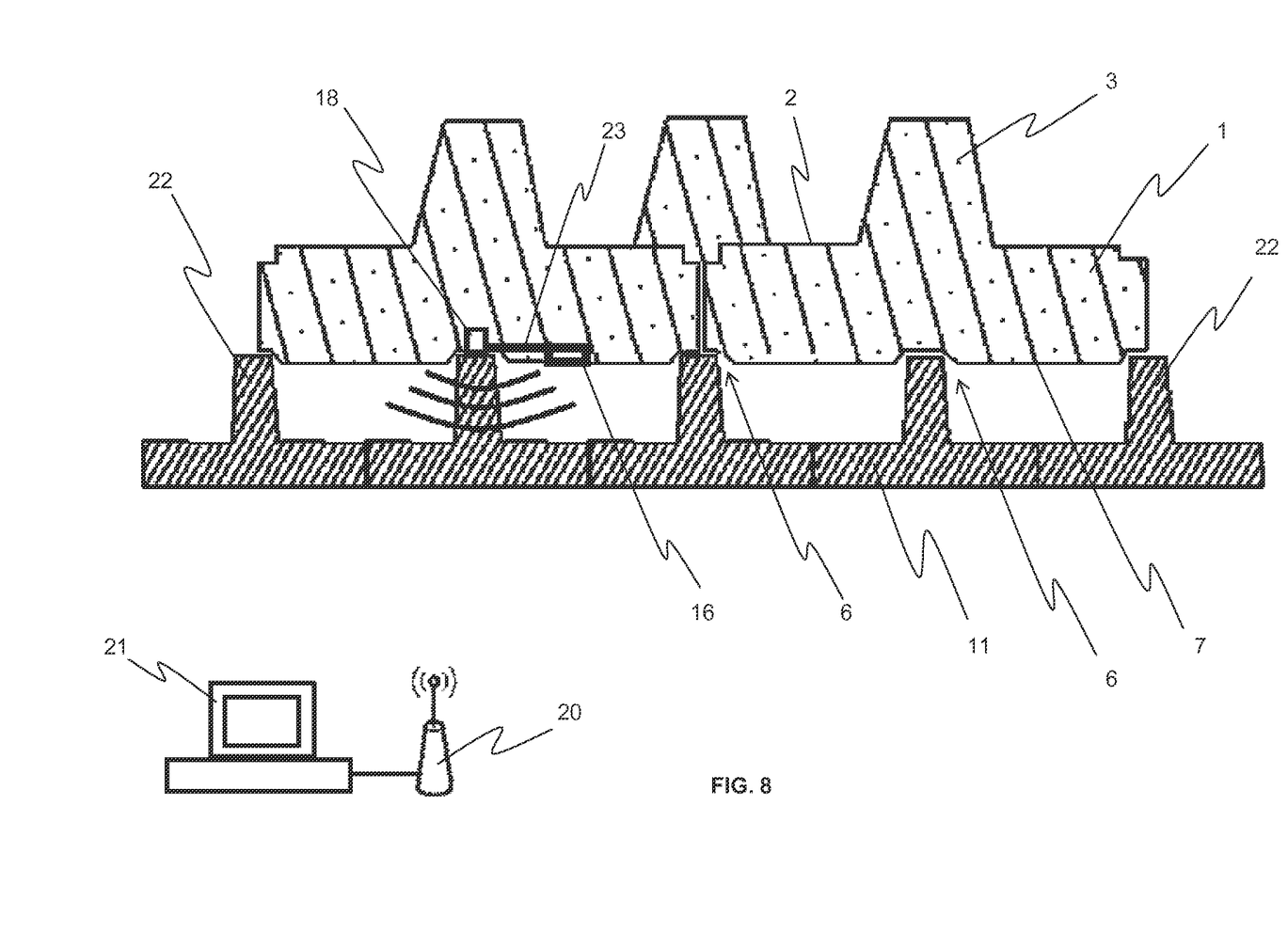
FIG. 8 shows a schematic view of a first location for the monitoring system sensor of the present invention.

In a second embodiment of the present invention as shown in FIG. 8, the signal from the accelerometer (16) is conveyed by wiring (23) located on the external surface (7) of the grate (1), wherein said wiring (23) reaches the trough (6) of the grate where the wireless transmitter (18) is placed, and wherein the wireless signal is output directly to the wireless receiver (20), where the signal is processed by a signal reader (21), usually a PC with a signal reader software. In this case, the wireless receiver (20) can also be placed in a safe area outside the SAG mill at a distance of approximately 20 meters from the mill.

In the second embodiment, the wireless signal from the transmitter (18) can be directly issued from the grate (1). While the second embodiment represents a rather simple embodiment of the invention to send the wireless signal, however said signal requires a greater number of field testing and testing inside the mill as to determine the correlation between the vibration received and thickness.

Figure 9:
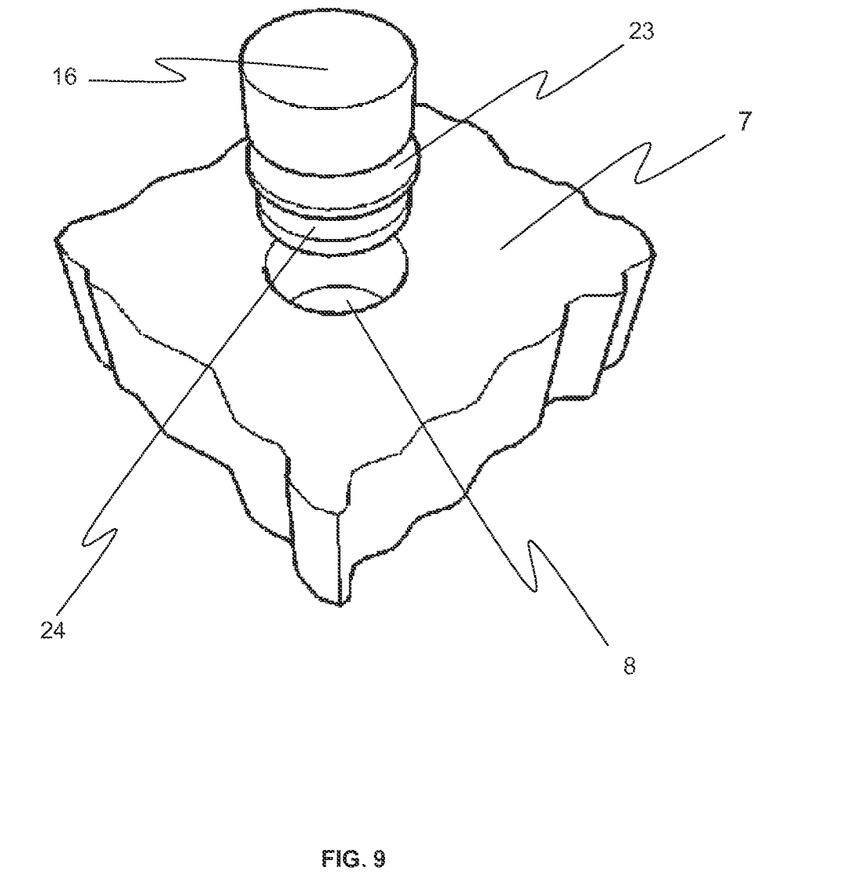
FIG. 9 shows a schematic perspective of the installation of the accelerometer in the grate.

Should the accelerometer (16) be installed in direct contact with the external surface (7) of the grate (1), upon impact it can be saturated which will result in the accelerometer moving off its scale thus rendering impossible to take measurement. Consequentially, the two modalities of the invention consider the accelerometer installed on the grate is done through elastomer material, such as rubber. FIG. 9 shows one of the preferred locations to mount the accelerometer of the monitoring system in the present invention. A bore (8) is made unto the external surface (7) of the grate (1), wherein the bore (8) has a sufficient depth as to accommodate a magnet (24) on its bottom part thereof and on to allow placing of a rubber (25) over the magnet (24) as to allow magnetic force to be exercised and, therefore adhesion of the accelerometer to the magnet (24) as to securely affix the grate to the accelerometer.

While is true that in the preferred description of the invention the accelerometer is used as the sensor from which the signals correlate to the thickness, it is possible to use other types of sensor that provide the same function, such as a strain gage.

Prior to mounting the grate (1) in a mill (9), it is necessary to calibrate the system. The calibration consists of:

(a) Subjecting the ribs (5) in the grate (1) to impacts using one of the balls (26) used in the mill (9).

b) Recording the signal using the signal reader (21).

c) Correlating said signal with the rib thickness (5).

Figure 10:
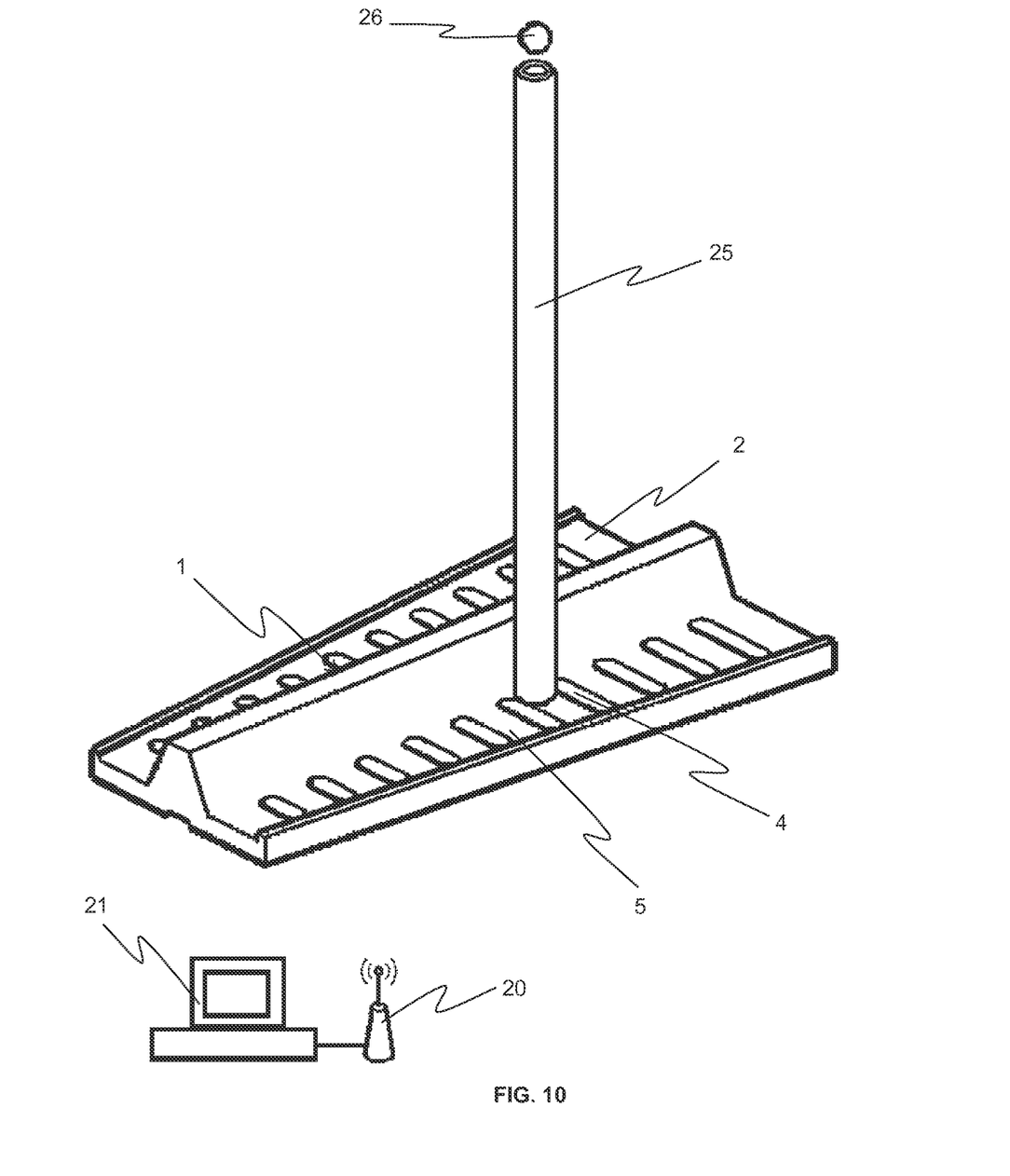
FIG. 10 illustrates a perspective view of the grate subject to calibration after being installed in the mill.

This procedure can be done with the grate inside the mill and, alternatively, outside of the mill. In this latter case (a), a tube (25), preferably made of plastic, is used wherein said tube has a diameter slightly greater than the ball (26), as shown in FIG. 10. This tube (25) is vertically placed where the lower end of said tube (25) is in contact or is placed slightly above the rib surface while the upper end receives the ball (26) through it, and where the vibration of the impact is captured by the sensor (16), wherein the sensor can be an accelerometer or a strain gage, that transmits the signal to the sensor adaptor unit (17) which comprises or functions as a transducer and to the wireless transmitter (18), wherein the wireless transmitter outputs the signal that is received by the wireless receiver (20) connected to a signal reader (21).

Should the grate be adjusted outside the mill, it should be placed inside the mill as to start the monitoring process.

Although embodiments of the invention have been shown and described, it is to be understood that various modifications, substitutions, and rearrangements of parts, components, equipment and method (process) steps as well as other uses for the invention can be made by those skilled in the art without departing from the novel spirit and scope of the invention.

The invention claimed is:

1. A real-time monitoring system to monitor wearing in thickness of ribs (5) of a grate (1) of a semi-autogenous (SAG) mill (9) due to abrasive action of tore pulp residing inside the mill and due to action of the grinding elements during operation of the mill, and which in certain cases also generates obstruction of slots (4) due to jamming of said grinding elements inside the slots (4) while the mill is running, and said grate (1) has a screening surface (2) that includes a pulp lifter (3) and an external surface (7) that is not exposed to impacts, and also includes a central trough (6) where the supporting elements fit and which allow securing the grate inside the mill through fitting bolts (12), WHEREIN said system includes:
   a sensor (16) placed on the external surface (7) of said grate (1);
   a wireless transmitter (18) connected to said sensor (16), wherein said transmitter outputs a signal from the sensor (16);
   a wireless receiver (20) for receiving the signal from the wireless transmitter (18);
   a signal reader (21) connected to said wireless receiver (20) to process signals received from the sensor;
   a ball (26) for use in the mill (9) for impacting the ribs (5) of the grate (1) to produce a vibration that is registered by a sensor (16) which transmits a signal to the wireless transmitter (18), and the wireless transmitter outputs the signal that is received by a wireless receiver (20) that is connected to a signal reader (21);
   recording means for recording the signal using the signal reader (21); and
   correlating means for correlating the signal with the ribs thickness (5); whereby
   the ball (26) cooperates with the ribs (5), sensor (16) wireless transmitter (18), recoding means, and correlating means as indicated above for calibrating the real-time monitoring system to monitor wearing in the thickness of the ribs of the grate (1) of the mill (9).

2. The monitoring system set forth in claim 1, WHEREIN said sensor (16) is a strain gage.

3. The monitoring system set forth in claim 1 WHEREIN said signal reader (21) is a PC with signal reader software.

4. The monitoring system set forth in claim 1 including a tube (25) with a diameter which is slightly greater than the diameter of the ball (26), which in said tube (25) is placed in a vertical position to the grate located outside of the mill, and the lower part of said tube (25) is in contact or is slightly located above a surface of the ribs surface and the ball is placed on top of the tube where it falls through it.

5. The monitoring system set forth in claim 1, WHEREIN said sensor (16) is an accelerometer.

6. The monitoring system set forth in claim 5 WHEREIN the signal from the sensor (16) is conveyed by wiring (23) located on the external surface (7) of the grate (1), and said wiring (23) reaches the trough (6) of the grate where the wireless transmitter (18) is placed, and the wireless signal is output directly to the wireless receiver (20), where the signal is processed by said signal reader (21).

7. The monitoring system set forth in claim 1 WHEREIN said sensor (16) and said wireless transmitter (18) are all connected to a timer (19) which defines a time interval to issue the signals from the transmitter.

8. The monitoring system set forth in any of the claim 7, WHEREIN the grate (1) defines a bore (8) with a sufficient depth as to accommodate a magnet (24) on its bottom part thereof and on to allow placing of a rubber (25) over the magnet (24) as to allow magnetic force to be exercised and, therefore adhesion of the sensor to the magnet (24) as to securely affix the grate to the sensor.

9. The monitoring system set forth in claim 1 WHEREIN the signal from said sensor (16) is conveyed by wiring (23) located on the external surface (7) of the grate (1), wherein said wiring (23) reaches the trough (6) of the grate (1) to then enter the chamber (15) located on the supporting elements (22), wherein said wiring (23) connects the wireless transmitter (18), and wherein the wireless signal is output to the wireless receiver (20), where the signal is processed by said signal reader (21).

10. The monitoring system set forth in claim 9 WHEREIN said wireless receiver (20) is placed in a safe area outside the SAG mill at a distance of approximately 20 meters from the mill.

11. A method to calibrate a real-time monitoring system to monitor wearing in thickness of ribs (5) of a grate (1) of a semi-autogenous (SAG) mill (9) due to abrasive action of ore pulp residing inside the mill and due to action of grinding elements during operation of the mill, and which in certain cases also generates obstruction of slots (4) due to jamming of the grinding elements inside the slots (4) while the mill is running, and the grate (1) has a screening surface (2) that includes a pulp lifter (3) and an external surface (7) that is not exposed to impacts, and also includes a central trough (6) where the supporting elements fit and which allow securing the grate inside the mill through fitting bolts (12), WHEREIN said method includes the following stages:
   a) submitting the ribs (5) of the grate (1) to impacts using a ball (26) that is used in the mill (9), wherein a vibration produced by the impact is registered by a sensor (16) which transmits a signal to a wireless transmitter (18), and the wireless transmitter outputs the signal that is received by a wireless receiver (20) connected to a signal reader (21);
   b) recording the signal using the signal reader (21); and
   c) correlating said signal with the ribs thickness (5).

12. The method to calibrate the monitoring system set forth in claim 11 WHEREIN the sensor (16) is an accelerometer.

13. The method to calibrate the monitoring system set forth in claim 11 WHEREIN the sensor (16) is a strain gage.

14. The method to calibrate a monitoring system set forth in claim 11, WHEREIN stage a) consists of using a tube (25) with a diameter which is slightly greater than the diameter of the ball (26), which in said tube (25) is placed in a vertical position to the grate located outside of the mill, and the lower part of said tube (25) is in contact or is slightly located above the ribs surface and the ball is placed on top of the tube where it falls through it (26).

15. The method to calibrate the monitoring system set forth in claim 14, WHEREIN the tube (25) is made of plastic material.

* * * * *